United States Patent
Anderson et al.

(10) Patent No.: US 7,775,206 B2
(45) Date of Patent: *Aug. 17, 2010

(54) NEONATE SUCTION CATHETER ASSEMBLY

(75) Inventors: Stephen A. Anderson, Thompson Station, TN (US); Richard C. Dowdy, Colleyville, TX (US)

(73) Assignee: Egret Medical Products, Inc., Garland, TX (US)

( * ) Notice: Subject to any disclaimer, the term of this patent is extended or adjusted under 35 U.S.C. 154(b) by 447 days.

This patent is subject to a terminal disclaimer.

(21) Appl. No.: 11/445,423

(22) Filed: Jun. 1, 2006

(65) Prior Publication Data

US 2007/0282250 A1 Dec. 6, 2007

(51) Int. Cl.
*A61M 16/00* (2006.01)
*A61M 15/00* (2006.01)

(52) U.S. Cl. .................. 128/205.19; 128/205.24; 128/207.14; 128/207.16; 128/200.26; 128/203.12; 604/116; 604/163; 604/171

(58) Field of Classification Search ............ 128/207.16, 128/200.26, 912, 207.14, 207.15; 604/119, 604/163, 171

See application file for complete search history.

(56) References Cited

U.S. PATENT DOCUMENTS

| | | | |
|---|---|---|---|
| 3,991,762 A | 11/1976 | Radford | |
| 4,569,344 A | 2/1986 | Palmer | |
| 4,825,859 A | 5/1989 | Lambert | |
| 4,836,199 A | 6/1989 | Palmer | |
| 4,850,350 A | 7/1989 | Jackson | |
| 4,872,579 A | 10/1989 | Palmer | |
| 5,073,164 A | 12/1991 | Hollister et al. | |
| 5,088,486 A | 2/1992 | Jinotti | |
| 5,255,676 A * | 10/1993 | Russo | 128/207.14 |
| 5,337,780 A | 8/1994 | Kee | |
| 5,354,267 A | 10/1994 | Niermann et al. | |
| 5,368,017 A | 11/1994 | Sorensen et al. | |
| 5,598,840 A | 2/1997 | Iund et al. | |
| 5,642,726 A | 7/1997 | Owens et al. | |
| 5,694,922 A | 12/1997 | Palmer | |
| 5,715,815 A | 2/1998 | Lorenzen et al. | |
| 5,730,123 A | 3/1998 | Lorenzen et al. | |
| 5,735,271 A | 4/1998 | Lorenzen et al. | |

(Continued)

OTHER PUBLICATIONS

International Search Report for Co-Pending PCT Application No. PCT/US2007/070096 Issued Sep. 11, 2008.

(Continued)

*Primary Examiner*—Tatyana Zalukaeva
*Assistant Examiner*—Clinton Ostrup
(74) *Attorney, Agent, or Firm*—Gardere Wynne Sewell, LLP (57) ABSTRACT

A suction catheter assembly, particularly adapted for neonatal use includes a distal manifold body including a rotatable connector for connection to an endotracheal tube, a ventilating port member and an ancillary catheter receiving port member. The manifold body is rotatably joined to a catheter tube seal housing. The seal housing includes an irrigation port member. A catheter tube wiper seal and a filter member are disposed in the seal housing which is joined to a suction control valve assembly by an elongated flexible sheath defining an enclosed space through which the catheter tube extends between the valve assembly and the manifold. A resilient closure member actuator and slide lock member are engageable with a closure member of the valve assembly.

24 Claims, 5 Drawing Sheets

U.S. PATENT DOCUMENTS

| | | |
|---|---|---|
| 5,775,325 A | 7/1998 | Russo |
| 5,919,174 A | 7/1999 | Hanson |
| 6,012,451 A | 1/2000 | Palmer |
| 6,070,582 A * | 6/2000 | Kee ................. 128/207.16 |
| 6,109,259 A | 8/2000 | Fitzgerald |
| 6,494,203 B1 | 12/2002 | Palmer |
| 6,543,451 B1 | 4/2003 | Crump et al. |
| 6,575,944 B1 | 6/2003 | McNary et al. |
| 6,579,254 B1 | 6/2003 | McNary et al. |
| 6,588,425 B2 | 7/2003 | Rouns et al. |
| 6,615,835 B1 | 9/2003 | Cise et al. |
| 6,729,326 B1 | 5/2004 | Winterton et al. |
| 6,923,184 B1 * | 8/2005 | Russo ................. 128/207.14 |
| 6,935,339 B2 | 8/2005 | Mattar et al. |
| 7,188,623 B2 * | 3/2007 | Anderson et al. ...... 128/207.16 |
| 2006/0005841 A1 | 1/2006 | Anderson et al. |

OTHER PUBLICATIONS

Written Opinion for Co-Pending PCT Application No. PCT/US2007/070096 Issued Sep. 11, 2008.

* cited by examiner

NEONATE SUCTION CATHETER ASSEMBLY

BACKGROUND OF THE INVENTION

Several developments have taken place with regard to providing suction catheter assemblies for use in obtaining respiratory tract secretions and in treating respiratory distress in infants and young children. Continued improvements have been sought for such suction catheter assemblies, including providing a catheter assembly which will reduce the chance of causing respiratory infections, to reasonably assure that the catheter suction control valve is not inadvertently left in an open position, preventing cross contamination to the caregiver using the catheter assembly, minimizing twisting and manipulation problems associated with using the catheter assembly, and related problems known to those skilled in the art.

There has also been a need for improvements in suction catheter assemblies for use in treating infants and young children which includes providing an access port for the administration of fluids using a second catheter tube to enable the user to have more options to administer treatment without disconnecting the apparatus from the patient thereby reducing the chances for contamination. Still further, there has been a need to develop respiratory suction catheter assemblies which are hermetically sealed without the use of solvents to secure the parts to each other, and catheter assemblies that include a housing or manifold including an irrigation port which is operable to be swiveled with respect to a manifold part to improve ease of use. To these ends the present invention has been developed, taking into account the improvements in suction catheter assemblies described and claimed in our copending U.S. patent application Ser. No. 11/175,627, filed Jul. 6, 2005, and assigned to the assignee of the present invention. The subject matter of U.S. patent application Ser. No. 11/175,627 is incorporated herein by reference.

SUMMARY OF THE INVENTION

The present invention provides an improved suction catheter assembly. In particular, the suction catheter assembly of the present invention is intended for extended use in infants and utilizes certain components treated with a non-leaching antimicrobial agent to reduce bacterial levels on components of the assembly. Such treated components may include a catheter tube, a flexible tapered sheath extending between a manifold assembly and a control valve assembly and enclosing the catheter tube, a seal support housing, a catheter tube wiper seal and a filter operable to permit air to circulate between an interior space formed by the flexible sheath and ambient atmosphere.

In accordance with other important aspects of the present invention, a neonate suction catheter assembly is provided which is constructed of materials which are suitable for use with imaging equipment, such as magnetic resonance imaging, x-ray or tomography scanning equipment. A suction control valve for the catheter assembly contains a slide lock mechanism that communicates to the user that the valve is secured in an off or closed position. A flexible tapered sheath is provided to facilitate handling and insertion and retrieval of a catheter tube. The tapered sheath enables a better "feel" for the user or operator with regard to facilitation of insertion of the catheter into an airway. In particular, a catheter tube insertion depth marking viewing "window" having magnifying capabilities is disposed on the manifold to facilitate reading of indicia on the catheter tube thereby indicating the degree of extension of the catheter tube into the patient's airway. The use of a multipart manifold provides the ability to swivel or rotate components of the catheter assembly with respect to each other to facilitate ease of connecting and maintaining the catheter properly oriented for the patient's comfort and proper use.

Those skilled in the art will further appreciate the above-mentioned advantages and superior features of the invention together with other important aspects thereof upon reading the detailed description which follows in conjunction with the drawings.

DETAILED DESCRIPTION OF A PREFERRED EMBODIMENT

In the description which follows, like parts are marked throughout the specification and drawing with the same reference numerals, respectively. The drawing figures are not necessarily to scale and certain features may be shown exaggerated in scale or in somewhat generalized or schematic form in the interest of clarity and conciseness.

Figure 1:
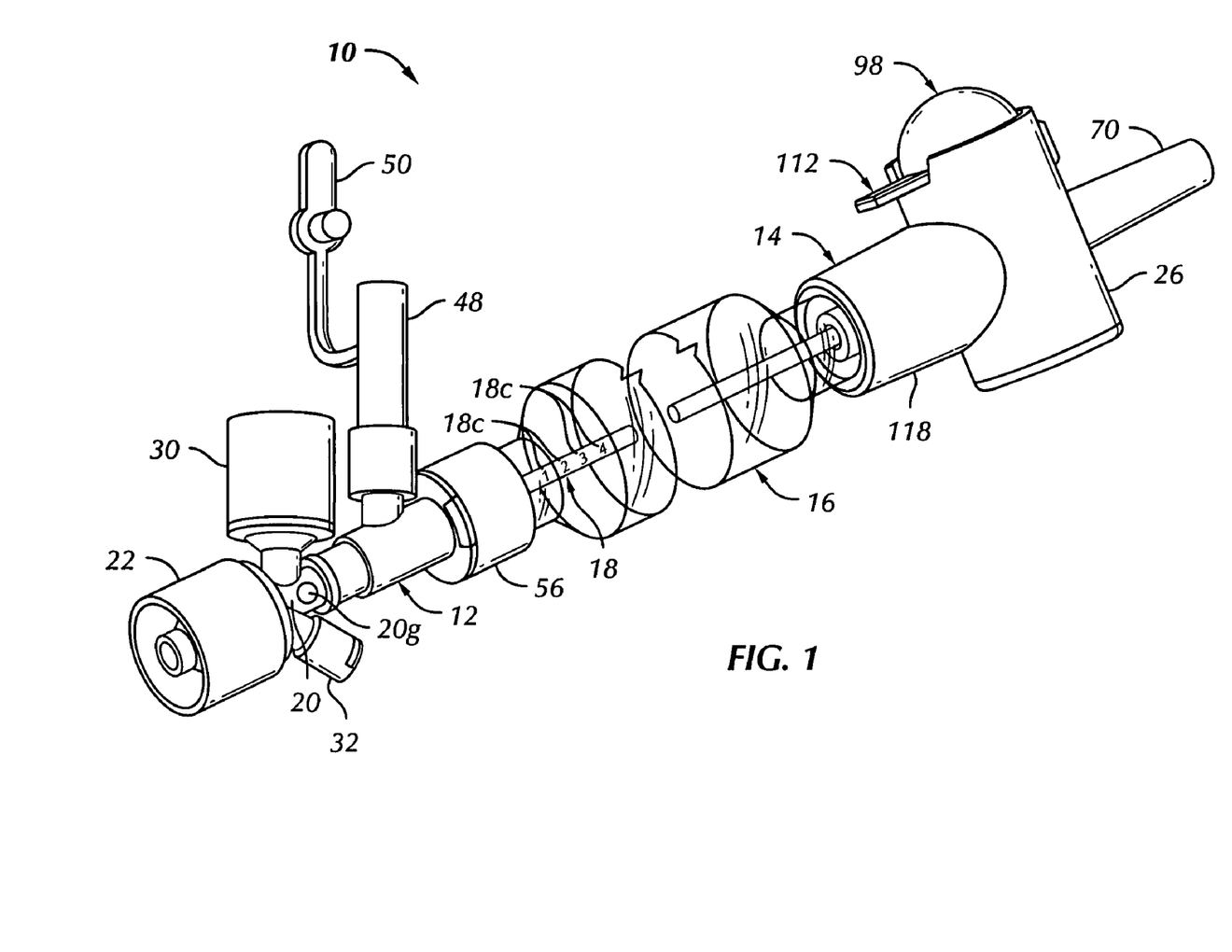
FIG. 1 is a perspective view of an improved suction catheter assembly in accordance with the present invention.

Referring now to FIG. 1, there is illustrated a suction catheter assembly, generally designated by the numeral 10, which is particularly adapted for treating infants and young children. The catheter assembly 10 includes a distal manifold assembly 12 connected to a suction control valve assembly 14 by an elongated, flexible sheath 16 and an elongated suction catheter tube 18 which extends from valve assembly 14 to manifold assembly 12 and is adapted to extend through the manifold assembly for insertion through an endotracheal tube or other device for treatment of the respiratory system of a patient, in a generally known manner. Accordingly, the catheter tube 18, which is essentially fixed with respect to the valve assembly 14, may be moved longitudinally through the manifold assembly 12 to extend into an area within the patient to be treated and withdrawn from such area also in a known manner and as described in our copending patent application referenced hereinabove. Moreover, the catheter assembly 10 is provided with several advantageous features which will be further appreciated by those skilled in the art from reading the further detailed description herein in conjunction with the drawings.

Figure 2:
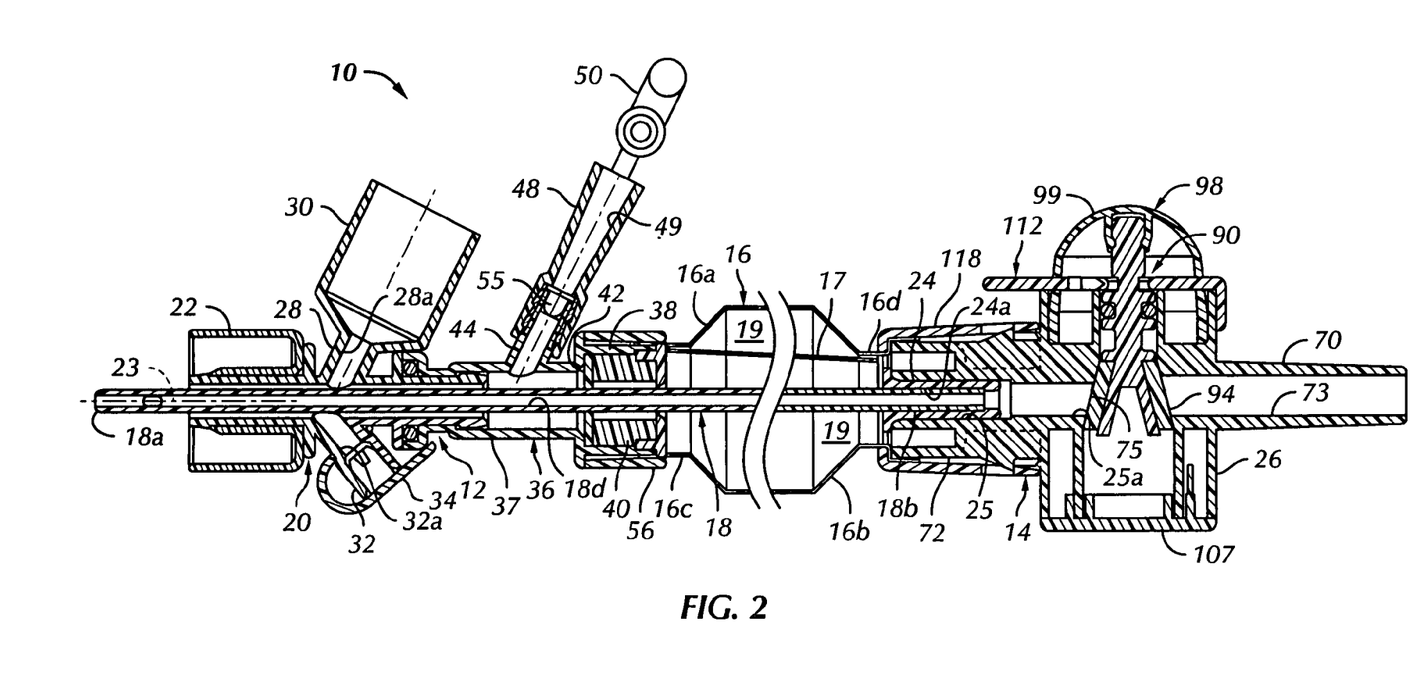
FIG. 2 is a longitudinal central section view of the catheter assembly shown in FIG. 1.

Referring now to FIG. 2, further details of the catheter assembly 10 are illustrated in a longitudinal central section view. The distal end manifold assembly 12 is characterized by a manifold body or member 20 which is adapted to support a generally cylindrical connector member 22 which is rotatable relative to the manifold body member about a longitudinal central axis 23. Axis 23 is also the central longitudinal axis of the catheter tube 18 which comprises an elongated, flexible, cylindrical tubular member formed of a suitable plastic material, such as polyvinylchloride or polyurethane and having a distal end 18a for insertion into an airway. The opposite end of catheter tube 18, generally designated by the numeral 18b, is forcibly insertable in a longitudinal bore 24a of a tubular retainer member 24 which, in turn, is forcibly inserted and suitably secured in a longitudinal bore 25 formed in a suction control valve housing member 26. Catheter tube 18 includes a central passage 18d extending therethrough.

Referring further to FIG. 2, manifold body member 20 includes a ventilator port member 28 integrally formed with the manifold member 20 and including an integral, enlarged diameter cylindrical shell-like connector part 30 for connecting the catheter assembly 10 to a ventilator tube, not shown. Opposite the ventilator port member 28 is a second integral port member 32 which projects at an acute angle opposite the ventilator port member 28 away from the body member 20 and is provided with a suitable flexible snap-in and out port closure member 34. Manifold body member 20 is also connected to a seal and filter support housing or member 36 characterized as a generally elongated tubular member having an enlarged diameter part 38 for receiving an annular air filter member 40 and a generally circular disk-like wiper seal member 42 engageable with the outer cylindrical surface of the catheter tube 18. A further port member 44 projects at an acute angle with respect to the generally tubular main body part 37 of the housing 36, as illustrated in FIGS. 2 and 3, and includes a separable tubular extension part 48 suitably secured thereto and having a flexible closure cap 50 integrally formed thereon for closing a passage 49 therein.

Figure 3:
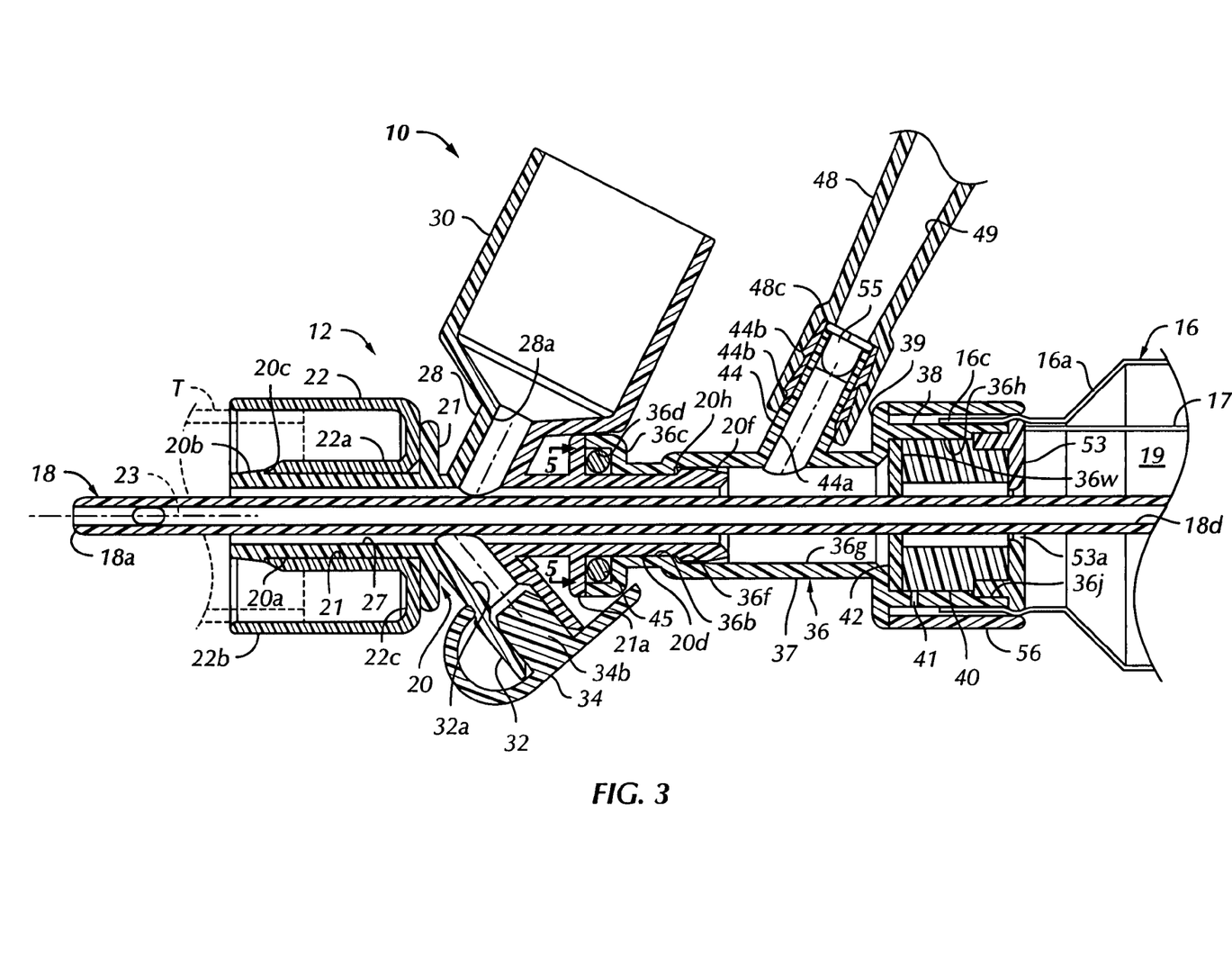
FIG. 3 is a longitudinal central section view of the manifold end of the suction catheter assembly on a larger scale.

Referring further to FIG. 3, additional details of the manifold assembly 12 are shown. Connector 22 includes an inner, cylindrical tubular hub part 22a having a bore 21 formed therein and integrally joined to an outer tubular sleeve part 22b by a transverse end wall 22c. Hub part 22 is adapted to be sleeved over a distal tubular body part 20a of manifold body member 20 and which includes an enlarged distal end portion 20b. Distal end portion 20b is slightly axially tapered to accommodate the sleeving of hub part 22a thereover and snapping the hub part 22a into a substantially axially locked position thanks to a transverse shoulder 20c formed as indicated in FIG. 3. In this way connector part 22 may be placed in its working position shown engageable with an integral transverse cylindrical flange 21 on manifold member 20, disposed between the shoulder 20c and the flange and freely rotatable relative to the body part 20a. Port members 28 and 32 include respective bores 28a and 32a which open into a central longitudinal bore 27 formed in manifold member 20. Bores 28a and 32a intersect bore 27 at acute angles of about sixty degrees and forty-five degrees, respectively, and bore 27 is of a larger diameter than the diameter of catheter tube 18, as indicated in FIG. 3 to allow catheter tube 18 to freely longitudinally extend within bore 27.

Figure 5:
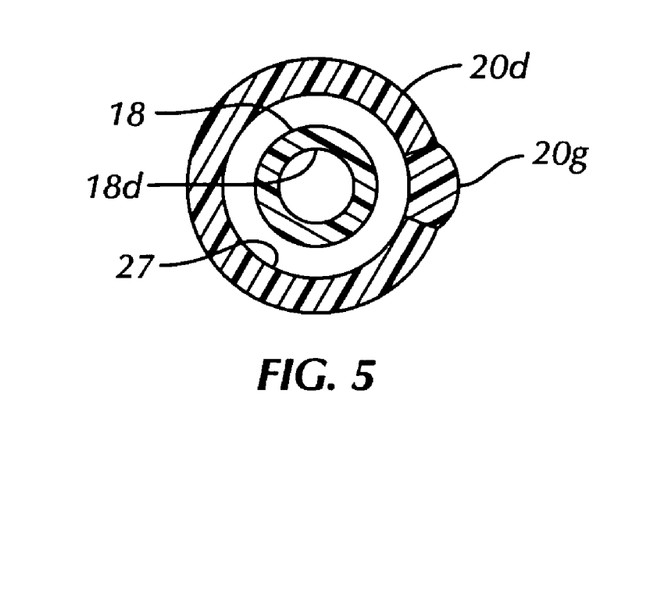
FIG. 5 is a detail section view taken from line 5-5 of FIG. 3.

Manifold body member 20 includes an integral body part 20d extending in a direction opposite the body part 20a and including a transverse cylindrical flange 21a formed thereon. Bore 27 extends through manifold body part 20d, as illustrated also in FIG. 5. Referring further to FIG. 5, manifold body part 20d is advantageously provided with an integral viewing port 20g which may comprise a window for viewing the catheter tube 18 and suitable indicia 18c formed thereon, see FIG. 1, whereby a user of the catheter assembly 10 may determine the extent to which the catheter tube has been inserted into a patient's airway. Viewing port or window 20g may be integrally formed of a suitable plastic which is used to form the manifold body member 20 or window 20g may be a separate part which is suitably secured to the manifold body part 20d and may have suitable magnification incorporated therein for ease of viewing the indicia 18c on catheter tube 18.

Referring further to FIG. 3, the body part 20d includes an enlarged diameter axially tapered distal end portion 20f forming a transverse shoulder 20h spaced from the flange 21a and adapted for receiving the seal housing 36 whereby the housing 36 includes a reduced diameter bore portion 36b and a distal transverse flange 36c forming an annular recess 36d for receiving an o-ring type seal 45. Flange 36c is operable to be disposed directly adjacent flange 21a when seal housing 36 is forcibly engaged with manifold body part 20d by sleeving the housing 36 over the body part 20d until the o-ring seal 45 engages flange 21a and shoulder 20h engages a cooperating shoulder 36f formed on housing 36 whereby housing 36 is secured axially to manifold member 20 but is freely rotatable with respect thereto about axis 23. In this way catheter assembly parts including valve assembly 14, sheath 16, seal support housing 36 and catheter tube 18 may rotate relative to manifold member 20 and vice versa. Moreover, since manifold body member 20 is rotatable relative to connector part 22, the catheter assembly 10 may be easily manipulated to reduce or eliminate any stress on a patient while the catheter assembly is attached to an endotracheal tube T, for sample, FIG. 3, and further while the catheter assembly is connected to ventilating equipment at the connector 30.

Referring still further to FIG. 3, seal housing 36, as previously described, is operable to retain filter 40 and annular seal 42 therein, both members being suitably treated with an anti-microbial agent to be described further herein. Annular seal 42 forcibly engages the outer circumference of catheter tube 18 to wipe same as the catheter tube is moved longitudinally through bore 27, a cooperating bore portion 36g of seal housing 36 and an enlarged bore portion 36h which receives the annular filter member 40 and the seal member 42 therein. Both members 40 and 42 are retained in housing 36 between a transverse wall 36w and a removable annular cap member 53 which is forcibly insertable within a counterbore 36j.

As further shown in FIGS. 2 and 3, the sleeve-like sheath 16 is preferably formed of a flexible, transparent plastic, such as polypropylene and suitably impregnated with the afore-mentioned anti-microbial agent. Sheath 16 includes tapered portions 16a and 16b extending opposite each other and tapered toward sheath distal end portions 16c and 16d, respectively. Sheath distal end portion 16d may be sleeved over seal housing hub part 38 and retained thereon by a cylindrical sleeve member 56 which is forcibly engageable with the hub part 38 and a transverse flange 39 delimiting same, as shown in FIG. 3. An elongated flexible tether 17 may extend within sheath 16, be of a type described in the aforementioned patent application and secured between the sleeve 56 and the hub 38 for limiting the distance that the valve assembly 14 may be moved away from manifold assembly 12 to avoid withdrawing the catheter tube 18 too far, such as beyond seal member 42.

Referring again to FIG. 3, the filter 40 is operable to allow the movement of air between an interior space 19, FIG. 2, formed by the sheath 16 and ambient atmosphere by way of the filter 40 and a port 41 formed in hub 38, as shown in FIG. 3. Sleeve 56, although forcibly retained on hub part 38, allows movement of air between ambient atmosphere and port 41 and thus between ambient atmosphere surrounding the catheter assembly 10 and the interior space 19. However, air moving between space 19 and ambient atmosphere surrounding the catheter assembly 10 is filtered and purified as it flows through filter 40 and also a bore 53a formed in cap 53, as shown in FIG. 3.

Referring still further to FIG. 3, the angular oriented port member 44 is provided with a suitable bore 44a intersecting bore 36g and being in communication with bore 27. Port member 44 is provided with annular exterior barbs 44b providing for forcible but releasable engagement with a hub part 48c of connector or extension member 48 so as to suitably retain these two members together. A so-called duckbill type check valve 55 is disposed in bore 44a to prevent flow of fluid from bore 44a into bore 49, but allowing the insertion of an irrigation fluid dispensing tube, not shown, to be inserted into bore 44a for cleaning catheter tube 18, as required. Thanks to the port members 32 and 44, ancillary devices may be inserted into bore 27 for selected purposes, including the aforementioned irrigation or cleaning of the catheter tube and the bores 27 and 36g.

Still further, ancillary catheter tubes, not shown, may be inserted through port member 32 and bore 27 for suitable treatment of a patient, when required. For example, closure plug 34b may be removed from bore 32a and an auxiliary catheter tube or the like inserted through bore 32a into and through bore 27 once catheter tube 18 has been withdrawn to the right, viewing FIG. 3, beyond the intersection of the bores 32a and 27. In this way, a patient may be treated in various ways without disconnecting the catheter assembly 10 from the patient and attaching a different catheter assembly to the patient. Again, thanks to the ability of the manifold body member 20 to rotate relative to the connector 22 and the seal housing 36, operations of the types aforementioned may be more easily and conveniently carried out without stress to the patient.

Figure 4:
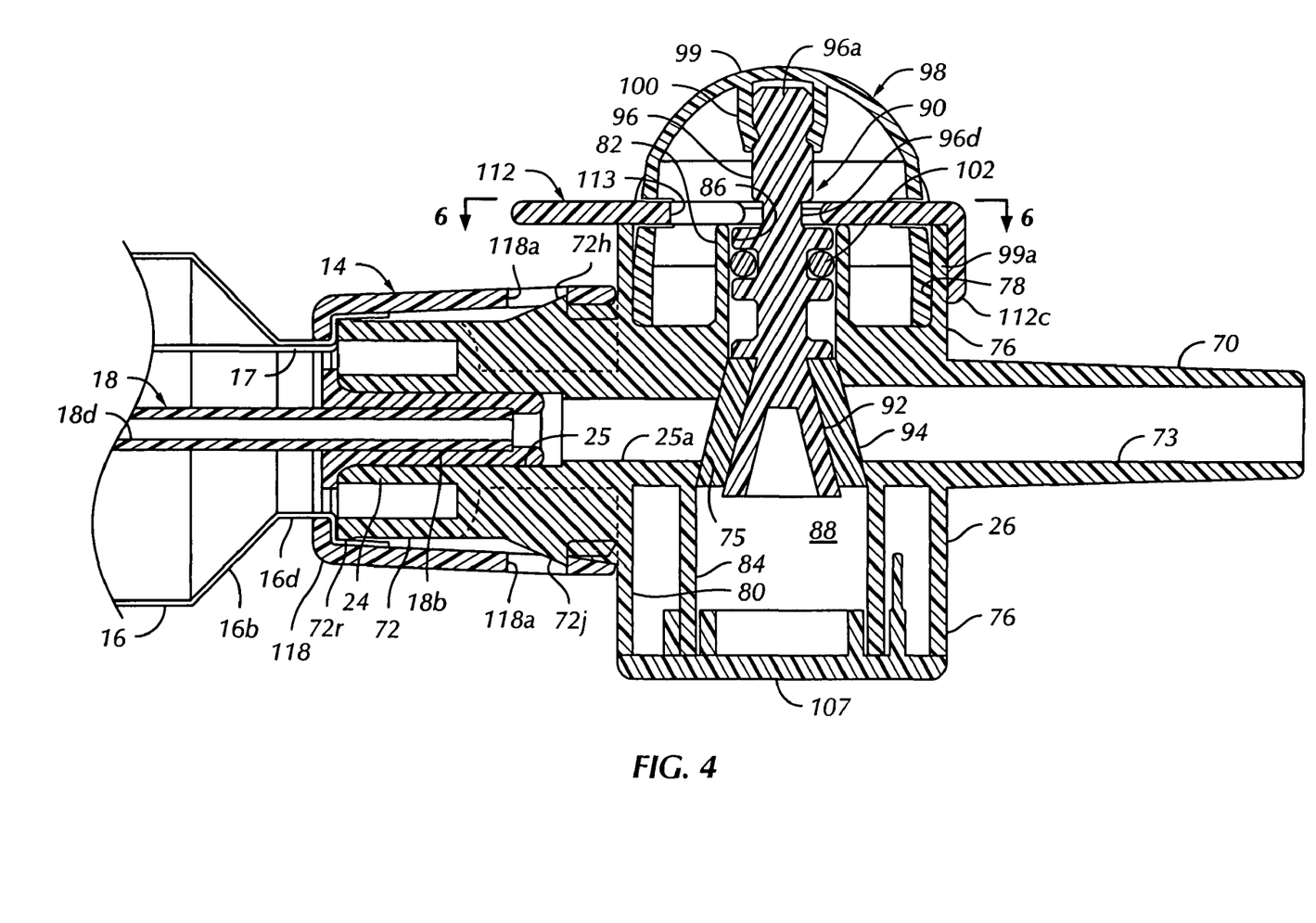
FIG. 4 is a longitudinal central section view of the valve assembly for the suction catheter assembly and also on a larger scale.

Referring now primarily to FIG. 4, suction control valve 14 is, as previously mentioned, characterized by a body 26 having an elongated generally cylindrical spigot part 70 aligned with and projecting in a direction opposite a generally cylindrical boss 72. An axial bore 73 extends through spigot part 70 and is intersected by a transverse frustoconical bore defined by a bore wall 75, FIG. 4, and which also intersects a passage 25a coaxial with bore 25 and bore 73. Housing 26 is further characterized by a cylindrical outer wall 76 which projects in opposite directions from spigot 70 and boss 72, as illustrated. Outer wall 76 defines a bore 78 and a bore 80 spaced from respective cylindrical tubular bosses 82 and 84, which define, respectively, an axial bore 86 and a chamber 88 for receiving a valve closure member 90. Closure member 90 includes a frustoconical head part 92 supporting a frustoconical seal member 94 and integrally joined to a stem part 96 which projects through bore 86 and is engaged with a generally cup-shaped valve actuator member 98. Actuator member 98 includes an arcuate head part 99 and an integral, depending cylindrical skirt 99a disposed snuggly in bore 78. Head part 99 includes an integral collar 100 forcibly engaged with the distal end 96a of stem 96. Actuator member 98 is formed of a suitable resilient material, such as polypropylene, and has an elastic memory which biases the closure member 90 in the position shown in FIG. 4, which is the valve closed position, whereby the seal member 94 is engaged with a valve seat formed by frustoconical bore wall 75. A suitable o-ring seal 102 is disposed around stem part 96 and is slidably engageable with the bore wall of bore 86. Housing 26 is also sealed at the portion defined by the wall 76 by a suitable cap 107, as shown in FIG. 4.

Figure 6:
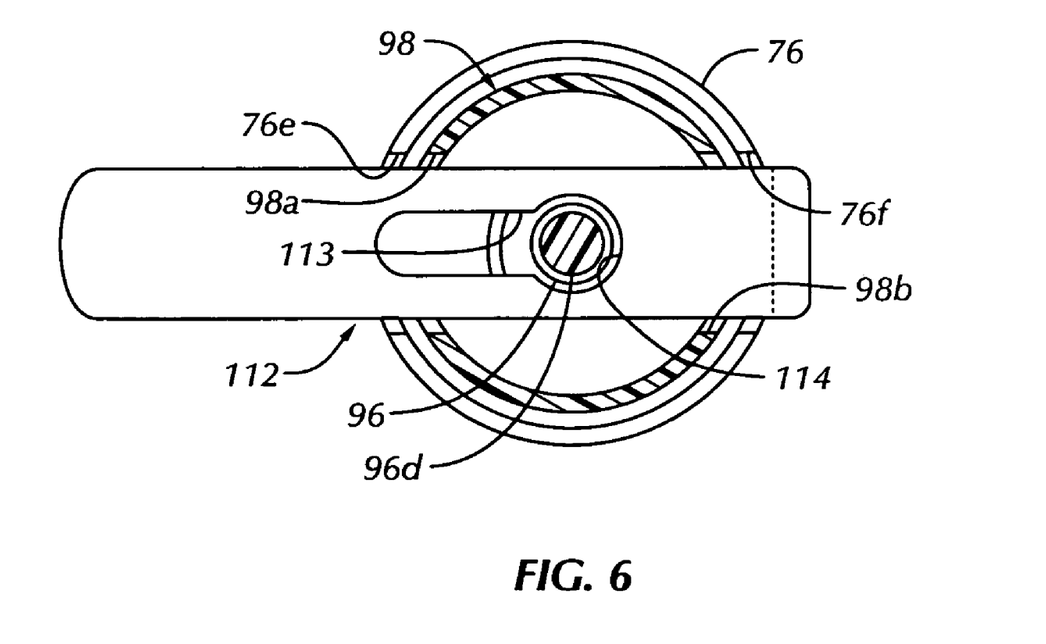
FIG. 6 is a detail view taken from line 6-6 of FIG. 4.

Actuator member 98 includes opposed slots 98a and 98b, FIG. 6, forming clearance for a slide-type lock member 112. Lock member 112 also extends within opposed cooperating slots 76e and 76f formed in housing outer wall 76. Slide lock member 112 includes a somewhat keyhole shaped slot 113, 114 for receiving closure member stem 96. The diameter of slot part 114 is large enough to form clearance for stem 96 while keyhole slot portion 113 is of a width slightly less than the diameter of stem 96. However, stem 96 includes a reduced diameter groove 96d which is receivable in slot 113 so that the valve closure member 90 may be locked in a closed position when the slide lock member 112 is moved to the right, viewing FIGS. 4 and 6. In the position of the slide lock member 112 shown in FIGS. 4 and 6, the closure member 90 may be moved to an open position by depressing the button type actuator member 98 and holding same in a selected working position. However, upon release of the actuator member 98, its elastic memory will bias the closure member 90 to the valve closed position shown in FIG. 4. Slide lock member 112 includes a depending tang portion 112c for limiting its movement and retaining the slide lock member in the limit position shown in FIGS. 4 and 6.

Referring further to FIG. 4, the body 26 of valve assembly 14 is provided with an annular, integral, radially outwardly projecting collar 72r on boss 72. A generally cylindrical sleeve-like retainer member 118 may be sleeved over the body part or boss 72 and engaged with opposed barbs 72h and 72j which are operable to register in slots 118a, respectively, in the sleeve 118 for retaining the sleeve engaged with the boss 72. As further illustrated in FIG. 4, the reduced diameter part 16d of sheath 16 and, preferably, one end of tether 17 are trapped between the sleeve 118 and annular collar 72r to retain the sheath firmly connected to the valve assembly 14. As previously mentioned catheter tube 18 is forcibly retained in engagement with elongated tubular retainer 24 which, in turn, is forcibly engaged with valve housing 26 at boss 72 by being a force fit within the bore 25. In this way, the catheter assembly 10 may be assembled without the use of chemical solvents to "weld" parts together, thanks to the design of the parts, as shown and described herein.

The catheter assembly 10 enjoys many of the advantages and superior features of the catheter assembly shown and described in U.S. patent application Ser. No. 11/175,627. For example, several of the parts of the catheter assembly 10 may be coated or otherwise treated with an anti-microbial agent in the same manner as describe in the aforementioned patent application. The manifold body member 20, the seal housing 36, the seal 42, the filter 40, the catheter tube 18 and the sheath 16, for example, may be treated with an anti-microbial agent such as one available from the BIOSAFE Division of Aegis, Pittsburgh, Pa., under the product designation AEM 5700. One procedure for obtaining parts, such as the body member 20, the seal housing 36, the seal 42, the filter 40 and the sheath 16 is to coat the resin particles used to form these parts with the above-mentioned agent prior to introducing the particles into an extrusion process, which may or may not include heating the particles to form a flowable mass that would be extruded or used to injection mold such parts. Alternatively, preformed parts may be coated with the aforementioned anti-microbial agent. A substantial number of the parts of the catheter assembly 10 may be formed of transparent material and, for example, also fabricated of the same materials used for corresponding parts as described in the aforementioned patent application.

Accordingly, those skilled in the art will recognize that the catheter assembly 10 enjoys several advantages in the art of respiratory suction catheter assemblies, including a suction control valve which requires positive actuation by the user and minimizes the chance of accidental actuation, particularly through suitable use of the slide lock member 112. The interior space delimited by the sheath 16 is subject to minimal or no contamination thanks to the seal 42 and the filter 40 and the purification process which takes place as air moves between the space 19 and ambient atmosphere surrounding the catheter assembly 10. The sheath 16 is configured to facilitate ease of handling thanks to the tapered end portions 16a and 16b which enable a better "feel" to the user to facilitate insertion of the catheter tube 18 into an actual or artificial airway. The angle of taper of portions 16a and 16b with respect to axis 23 may be in a preferred range of about thirty degrees to sixty degrees. The access port 32 is advantageous for enabling a user to have several options to administer treatment to a patient without disconnecting the catheter assembly 10 from the patient. Ease of use is also facilitated by the connector 22 which may swivel relative to the manifold body member 20. The seal housing 36 may also advantageously rotate or swivel relative to the manifold body member 20, thus, the seal housing the sheath 16, the suction control valve assembly 14 and catheter tube 18 are rotatable also relative to the manifold body member. As previously mentioned, the parts of the catheter assembly 10 may be forcibly connected to each other while still allowing for the functional requirements of the respective parts without the use of chemical solvents or weld processes often used with plastic structures. Still further, the ease of use of the catheter assembly 10 is enhanced by the indicia 18c on the catheter tube and the viewing window 20g.

Although a preferred embodiment of the invention has been described in detail, those skilled in the art will also recognize that various substitutions and modifications may be made without departing from the scope and spirit of the appended claims.

What is claimed is:

1. A suction catheter assembly for connection to an endotracheal tube for treating a patient, comprising:
   a suction control valve assembly;
   an elongated catheter tube connected at one end to said suction control valve assembly;
   a unitary manifold having a manifold body and opposed axially projecting boss parts and an elongated hollow bore extending through said manifold body;
   a connector member sleeved over one of said boss parts and retained on said one boss part for rotation relative to said manifold body;
   a seal housing connected to the other of said boss parts and rotatable relative to said manifold body;
   an elongated sheath interconnecting said suction control valve assembly and said seal housing and forming an enclosed space for extension of said elongated catheter tube therethrough, said elongated sheath being flexible and collapsible for extending said suction control valve assembly and said catheter tube toward said manifold body to insert said elongated catheter tube through said endotracheal tube; and
   plural port members formed on at least one of said manifold body and said seal housing for communicating fluids to and from said elongated hollow bore in said manifold body;
   wherein said suction control valve assembly includes a valve housing including a spigot for connection to a source of vacuum, a boss extending in a direction opposite said spigot, passage means in said boss and in said spigot forming a flow path for fluids passing into said valve housing from said elongated catheter tube, a tapered bore intersecting said passage means and a tapered plug closure member disposed in said tapered bore and engageable with a bore wall of said tapered bore.

2. The catheter assembly set forth in claim 1 including:
   a fluid filter supported in said seal housing and allowing fluid flow communication between said enclosed space and ambient atmosphere.

3. The catheter assembly set forth in claim 2 including:
   a seal member disposed in said seal housing and engageable with said elongated catheter tube when said elongated catheter tube is inserted in and withdrawn from said endotracheal tube.

4. The catheter assembly set forth in claim 3 wherein:
   at least one of said seal housing, said elongated catheter tube, said filter, said seal member and said elongated sheath is at least one of coated with and impregnated with an anti-microbial agent.

5. The catheter assembly set forth in claim 1 wherein:
   said connector includes a hub part and said one boss of said manifold body includes an integral collar engageable with said hub part for retaining said connector on and rotatable relative to said manifold body.

6. The catheter assembly set forth in claim 1 wherein:
   said seal housing and said other boss include cooperating projections thereon and engageable with each other to retain said seal housing connected to said manifold body and rotatable relative to said manifold body.

7. The catheter assembly set forth in claim 6 wherein:
   said seal housing includes a seal member engageable with a flange on said manifold body for forming a hermetic seal between said manifold body and said seal housing.

8. The catheter assembly set forth in claim 1 including:
   a port member formed integral with said seal housing and extending at an acute angle with respect to an axial bore of said seal housing which is aligned with and in communication with said bore in said manifold body.

9. The catheter assembly set forth in claim 1 wherein:
   said manifold body includes a first port member extending at an acute angle with respect to an axis of said manifold body and an integral connector part for connection to a ventilator.

10. The catheter assembly set forth in claim 1 wherein:
    said elongated sheath includes at least one tapered end portion and a portion sleeved over a part of said seal housing for retention thereon.

11. The catheter assembly set forth in claim 10 wherein:
    said elongated sheath includes a second tapered end portion at an opposite end of said elongated sheath for connection to a boss formed on a valve housing of said suction control valve assembly.

12. The catheter assembly set forth in claim 11 including:
    a sleeve engageable with said boss on said valve housing for securing said elongated sheath to said valve housing.

13. The catheter assembly set for forth in claim 1 where:
    said suction control valve assembly includes a resilient actuator member disposed on said valve housing and engageable with said closure member for biasing said closure member in a valve closed position, said actuator member including an arcuate head part engageable for moving said closure member from a closed position to a selected valve open position.

14. The catheter assembly set forth in claim 1 including:
    a window in one of said manifold and said seal housing operable for viewing indicia on said elongated catheter tube.

15. The catheter assembly set forth in claim 14 wherein:
    said window is configured to provide optical magnification to a person viewing said indicia through said window.

16. A suction catheter assembly for connection to an endotracheal tube for treating a patient, comprising:
    a suction control valve assembly;
    an elongated catheter tube connected at one end to said suction control valve assembly;

a unitary manifold having a manifold body and an elongated hollow bore extending therethrough;

a connector member retained on and operable for rotation relative to said manifold body;

a seal housing connected to and rotatable relative to said manifold body;

an elongated sheath interconnecting said suction control valve assembly and said seal housing and forming an enclosed space for extension of said elongated catheter tube therethrough, said elongated sheath being flexible and collapsible for extending said suction control valve assembly and said elongated catheter tube toward said manifold body to insert said elongated catheter tube through said endotracheal tube;

a seal member disposed in said seal housing and engageable with said elongated catheter tube when said elongated catheter tube is inserted in and withdrawn from said endotracheal tube; and a fluid filter supported in said seal housing and allowing fluid flow communication between said enclosed space and ambient atmosphere wherein said suction control valve assembly includes a valve housing including a spigot for connection to a source of vacuum, a boss extending in a direction opposite said spigot, passage means in said boss and in said spigot forming a flow path for fluids passing into said valve housing from said elongated catheter tube, a tapered bore intersecting said passage means and a tapered plug closure member disposed in said tapered bore and engageable with a bore wall of said tapered bore.

17. The catheter assembly set forth in claim 16 including:
plural port members formed on at least one of said manifold body and said seal housing for communicating fluids to and from said elongated hollow bore in said manifold body.

18. The catheter assembly set forth in claim 17 wherein:
at least one of said seal housing, said elongated catheter tube, said filter, said seal member and said elongated sheath is at least one of coated with and impregnated with an anti-microbial agent.

19. The catheter assembly set forth in claim 16 wherein:
said connector member includes a hub part and said manifold body includes an integral collar engageable with said hub part for retaining said connector on and rotatable relative to said manifold body.

20. The catheter assembly set forth in claim 16 wherein:
said seal housing and said manifold body include cooperating projections thereon and engageable with each other to retain said seal housing connected to and rotatable relative to said manifold body.

21. The catheter assembly set forth in claim 20 wherein:
said seal housing includes a seal member engageable with a flange on said manifold body for forming a hermetic seal between said manifold body and said seal housing.

22. The catheter assembly set forth in claim 16 including:
a window in one of said manifold and said seal housing operable for viewing indicia on said catheter tube.

23. The catheter assembly set forth in claim 22 wherein:
said window is configured to provide optical magnification to a person viewing said indicia through said window.

24. The catheter assembly set for forth in claim 16 where:
said suction control valve assembly includes a resilient actuator member disposed on said valve housing and engageable with said closure member for biasing said closure member in a valve closed position, said actuator member including an arcuate head part engageable for moving said closure member from a closed position to a selected valve open position.

\* \* \* \* \*